United States Patent
Biedermann et al.

[11] Patent Number: 6,102,949
[45] Date of Patent: Aug. 15, 2000

[54] INTERVERTEBRAE IMPLANT

[75] Inventors: Lutz Biedermann, VS-Villingen; Jürgen Harms, Waldbronn, both of Germany

[73] Assignee: Biedermann Motech GmbH, VS-Schwenningen, Germany

[21] Appl. No.: 09/200,885

[22] Filed: Nov. 30, 1998

[30] Foreign Application Priority Data

Dec. 3, 1997 [DE] Germany ............... 197 53 685

[51] Int. Cl.[7] ........................................... A61F 2/44
[52] U.S. Cl. ........................................................ 623/17
[58] Field of Search ........................ 623/16, 17, 18; 606/61

[56] References Cited

U.S. PATENT DOCUMENTS

| | | | |
|---|---|---|---|
| 4,599,086 | 7/1986 | Doty | 623/17 |
| 4,904,268 | 2/1990 | Alvarado | 623/23 |
| 5,123,926 | 6/1992 | Pisharodi | 623/17 |
| 5,454,811 | 10/1995 | Heubner | 606/72 |
| 5,632,748 | 5/1997 | Beck, Jr. et al. | 606/72 |
| 5,658,335 | 8/1997 | Allen | 623/23 |
| 5,800,547 | 9/1998 | Schafer et al. | 623/17 |
| 5,888,228 | 3/1999 | Knothe et al. | 623/17 |

FOREIGN PATENT DOCUMENTS

| | | |
|---|---|---|
| 44 16 605 C1 | 6/1995 | Germany. |
| 195 29 605 C2 | 2/1997 | Germany. |
| 195 49 426 C2 | 2/1997 | Germany. |

*Primary Examiner*—David J. Isabella
*Attorney, Agent, or Firm*—Geroge W. Neuner; Dike, Bronstein, Roberts and Cushman LLP

[57] ABSTRACT

An intervertebrae implant comprises two spaced sidewalls 1, 2, a front wall connecting the sidewalls at one end thereof, a back wall connecting the other end of the sidewall and corresponding apertures in the bottom and top surfaces extending transversely to the above-defined walls. In order to lock the implant in a desired position between two adjacent vertebrae a screw 13, 13' is rotatably provided in the front or back wall 3, 4, resp., and adapted to have a portion projecting beyond the bottom or top surface, resp., in a first rotational position and no projecting portion in a second rotational position.

11 Claims, 2 Drawing Sheets

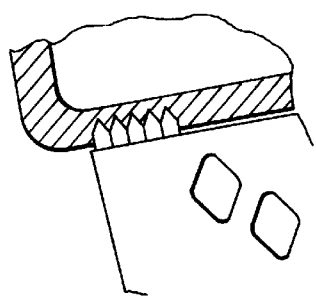
FIG.10
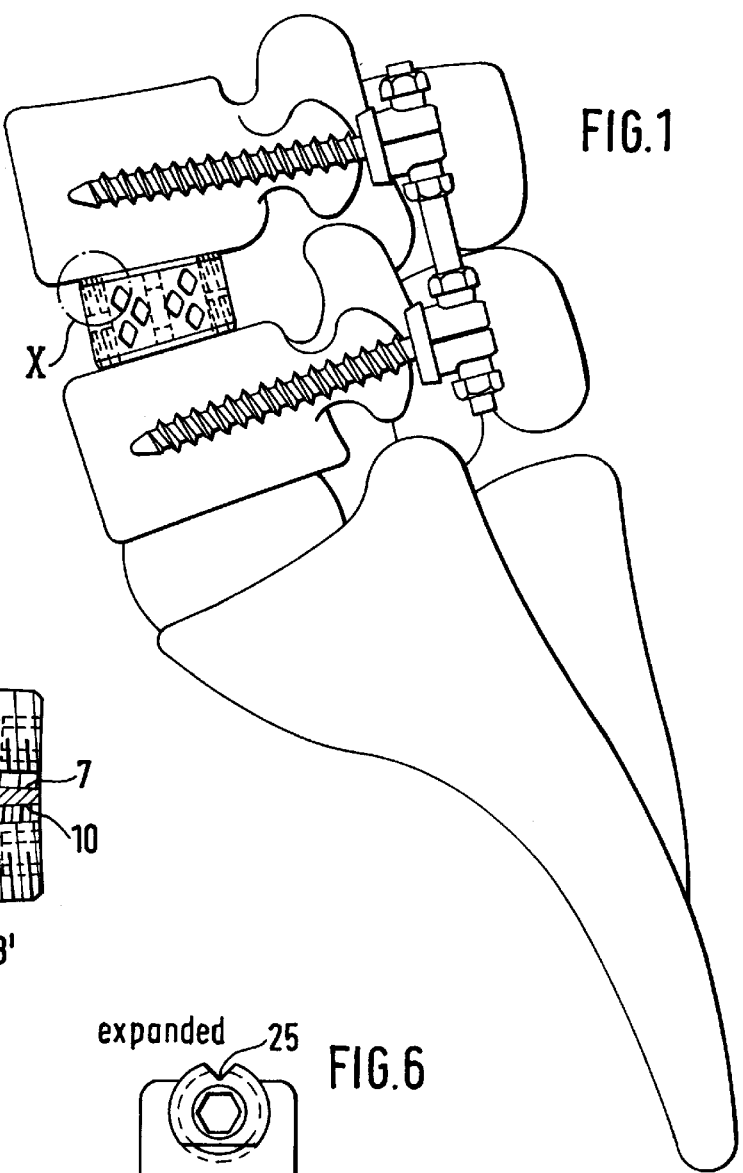
FIG.1
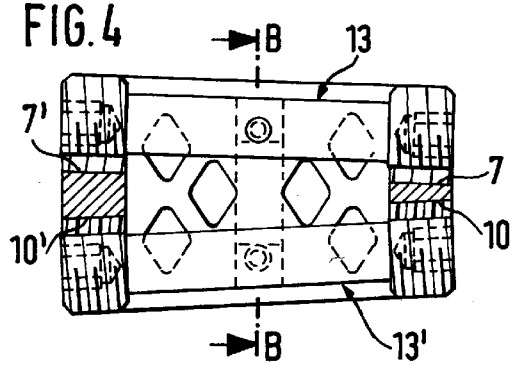
FIG.4
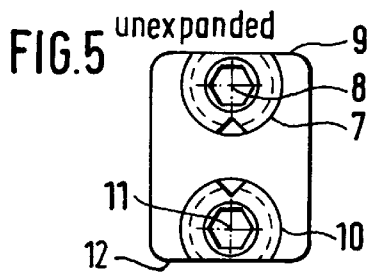
FIG.5 unexpanded
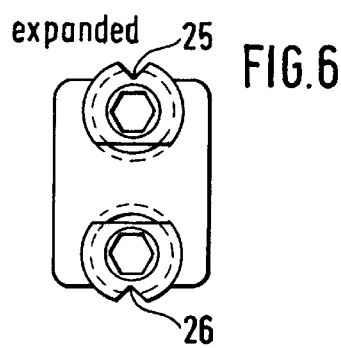
FIG.6 expanded
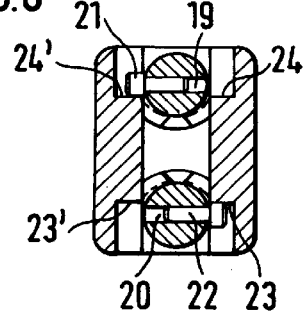
FIG.8 stop system
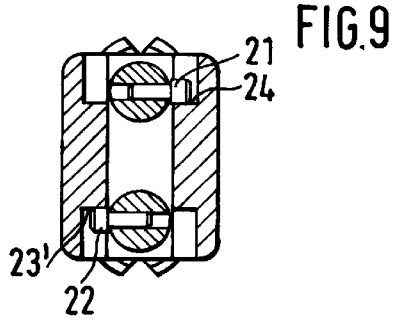
FIG.9 B-B

INTERVERTEBRAE IMPLANT

The invention relates to an intervertebrae implant comprising two sidewalls spaced from each other, a front wall connecting the sidewalls at one of their ends, a back wall connecting the sidewalls at their opposite other end and a corresponding aperture in the bottom and top surfaces extending transversely to the above-mentioned walls.

A corresponding intervertebrae implant is disclosed in DE 195 29 605 C. The implant comprises two hook-shaped portions which are first bent back into a cavity and, after inserting the implant between two vertebrae, moved outwards into an engaging position by screwing-in a screw having a cone-shaped portion. It is a particular disadvantage of this apparatus that the gripper arms can not be returned into their retracted position whereby the surgeon can not change the position of the implant after having advanced the gripping arms.

The DE 195 49 426 C discloses an intervertebrae implant wherein two terminal portions of a hollow body are moved from a previously folded position into a spread position by inserting a screw having a truncated cone-shaped portion.

The outside of the terminal portions comprises teeth which, in the spread position, engage the adjacent vertebrae. Again, there is the disadvantage that, after a first spreading and engagement of the teeth with the adjacent vertebrae, replacement or readjustment by retracting the teeth is impossible.

It is the object of the invention to provide an improved intervertebrae implant of the initially described kind.

This object is achieved by the intervertebrae implant defined in claim 1.

Further embodiments of the invention are defined in the subclaims.

Further features and advantages of the invention will be apparent from the description of an embodiment with reference to the Figures. In the Figures:

FIG. 1 is a side view of a portion of the spinal column with an inserted intervertebrae implant;

FIG. 4 is a side view, partially in sectional representation along line IV—IV, with screws;

FIG. 5 is a front view including screws in retracted position;

FIG. 6 shows the front view with screws in projecting position;

FIG. 8 shows a section along line B—B with screws in retracted position;

FIG. 9 a corresponding sectional representation with screws in projecting position; and FIG. 10 a detail of FIG. 1 in enlarged representation.

Figure 2:
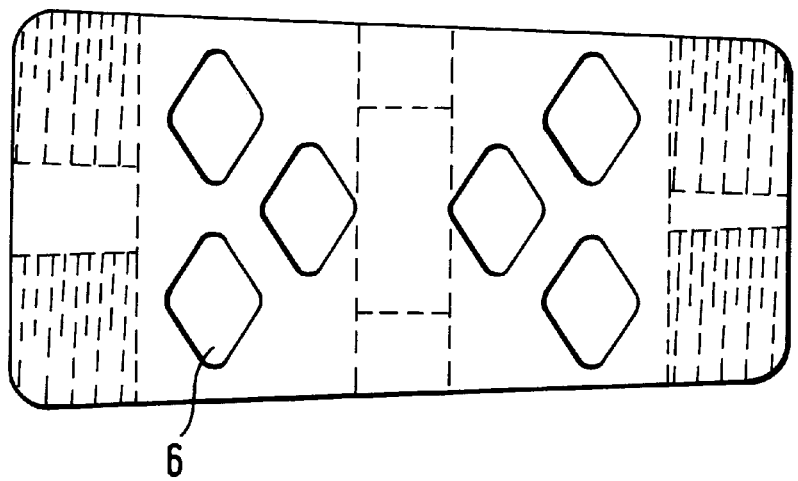
FIG. 2 is a side view of the intervertebrae implant without screws.
Figure 3:
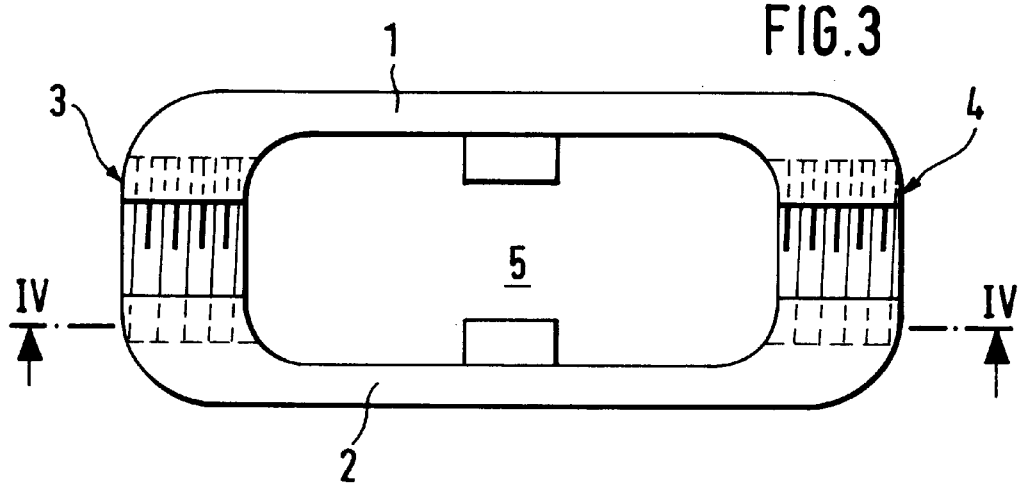
FIG. 3 is a top view of the intervertebrae implant without screw.

As best shown in the FIGS. 2 and 3 the implant comprises a first sidewall 1, an opposite second sidewall 2 spaced from the first sidewall, a front wall 3 connecting both sidewalls at their one end and a back wall 4 opposite to the front wall for connecting both sidewalls at their opposite other ends. As best shown in FIG. 3 the bottom and top surfaces are open so that the four walls surround a cavity 5 having an open top and bottom. As best shown in FIG. 2 the two sidewalls 1 and 2 have a plurality of preferably diamond-shaped holes 6 distributed over the wall surfaces.

As best shown in the FIGS. 4 to 9, the front wall 3 and the back wall 4 each have, in the center between the sidewalls, coaxially aligned threaded bores 7. The center 8 of the threaded bores is spaced from the upper edge 9 of the front and rear wall, resp., by a distance which is greater than 0 and smaller than the free width of the threaded bore. Moreover, a corresponding pair of threaded bores 10 is provided in the center of front wall and rear wall close to the lower edge 12. The center 11 of these threaded bores is spaced from the lower edge 12 by a distance which is greater than 0 and smaller than the radius of the free width of the bore 10.

Figure 7:
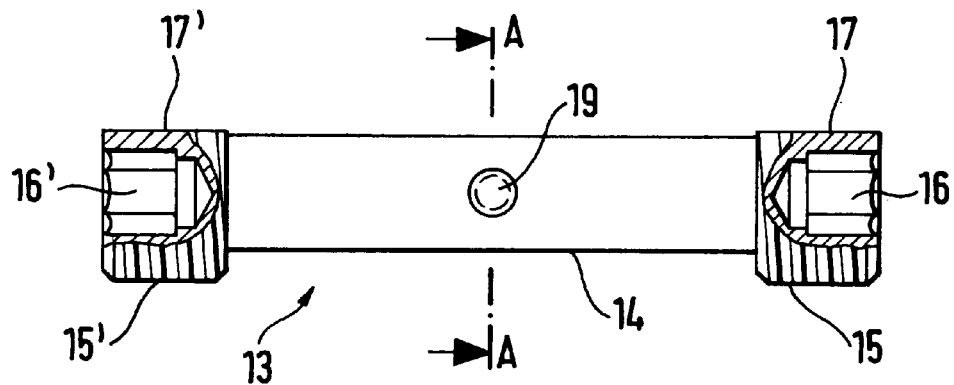
FIG. 7 is an enlarged side view of the screw.

A corresponding screw 13, 13' best represented in FIG. 7 is inserted into each pair of upper and lower threaded bores 7, 7' and 10, 10', resp. The screw has a middle shaft 14 and threaded portions 15, 15' provided at both opposite ends of the shaft and corresponding to each other. The threads of the threaded portions correspond to the threads of the threaded bores 7, 10. The diameter of the shaft is reduced so as to be displaceable within the threaded bore.

The threaded portions 15, 15' each have a front face provided with means for engagement of a screw driver. The embodiment shown has a corresponding hexagon socket 16, 16'. As best shown in the FIGS. 5 to 9 a corresponding segment-shaped portion is removed from one side of both threaded portions so as to form a plane surface 17, 17' and 18, 18', resp., extending perpendicular to a radius and having a distance from the center which equals the distance of the center from the upper and lower edge, resp. Each screw further comprises, as best shown in the FIGS. 7 to 9, a bore 19, 20 extending through the central axis in the longitudinal center of the screw. A corresponding set screw 21, 22 is screwed into these bores so that the head of the screws projects from the shaft. The axis of the bores 19, 20 extends parallel to the corresponding plane surfaces 17, 17' and 18, 18'. Furthermore, the plane surfaces 17 and 18 are parallel to the corresponding surfaces 17' and 18'.

As best represented in FIGS. 3, 8 and 9 the opposite sidewalls 1, 2 have, in their longitudinal center, corresponding pairs of stops 23, 23', 24, 24' seen from the upper edge 9 and from the lower edge 12, resp. The distance of the pairs of stops from the upper edge and lower edge, resp. is such that the plane surfaces 17, 17' and 18, resp. are aligned with the corresponding plane of the top and bottom surface, when the set screws 21, 22 abut the corresponding stop in the manner shown in FIG. 8.

As best shown in the FIGS. 5 to 9 the threaded portions 15, 15' each have a V-shaped recess 25, 26 provided at the diameters extending perpendicular to the plane surfaces 17, 17'. The base of each V-shaped recess is directed towards the center of the screw. The angle included by the two legs of the V-shaped recess is preferably between 60 and 100°. As shown in the FIGS. 8 and 9 the stops 23, 23' and 24, 24' are arranged in pairs so that the threaded portions with the V-shaped recesses therein project beyond the upper and lower edges, resp. in the second rotational position of the screws which is shown in FIG. 9 and defined by abutment of the set screws on the stops 24 and 23'.

As shown in the FIGS. 2 and 4 the two sidewalls 1 and 2 of the shown embodiment have a trapezoidal shape tapering from the front wall 3 towards the back wall 4 so as to make the implant wedge-shaped with a predetermined wedge angle.

In operation two screws 13, 13' are first rotated into the position shown in FIG. 1 wherein the threaded portions do not project beyond the upper and lower edge and therefore the top and bottom surface, resp. Thereafter the implant is inserted between the adjacent vertebrae into the position shown in FIG. 1. Thereupon the two screws 13, 13' are rotated by 180 degrees from the position shown in FIGS. 5 and 8 into the position shown in the FIGS. 6 and 9 whereby the corresponding thread having the V-shaped recess therein projects beyond the upper edge and lower edge or top and bottom surface, resp., in the manner shown in the FIGS. 6 and 9. This results in an engagement of the implant with the end plate of the adjacent vertebra and in a desired lock of the implant relative to the vertebrae, as best shown in FIG. 10. In order to obtain a safe engagement without weakening the end plate of the vertebra more than necessary the distance of the centers 8 and 11 from the upper and lower edge, resp., is preferably about 1.5 mm smaller than the radius of the bore 7.

Preferably, the implant is made of titanium. Its inner cavity is filled with bone material before insertion so as to enhance growing through and together.

What is claimed is:

1. An intervertebrae implant comprising a hollow body defined by a first sidewall, a second sidewall spaced from said first sidewall, a front wall connecting said first and second sidewalls at one end thereof, a back wall connecting said first and second sidewalls at their other end, and having open top and bottom surfaces, and screw means supported in said front or back wall for rotation from a first rotational position into a second rotational position, said screw means having a member projecting beyond said top or bottom surface in said first rotational position and not projecting beyond said top or bottom surface in said second rotational position of said screw means.

2. The intervertebrae implant of claim 1, comprising means for rotatably supporting said screw means in said front and back wall, said screw means extending from said front wall to said back wall and having one end supported in said front wall and another end supported in said back wall.

3. The intervertebrae implant of claim 2, wherein both ends of said screw means comprise engagement apertures for insertion of a screw driver.

4. The intervertebrae implant of claim 1, wherein said screw means comprises a threaded portion forming said projecting member in said first rotational position.

5. The intervertebrae implant of claim 1, comprising first screw means provided adjacent to said top surface and second screw means provided adjacent to said bottom surface.

6. The intervertebrae implant of claim 1, comprising first stop means provided in an interior of said hollow body for engagement with a projection provided at said screw means in said first rotational position of said screw means.

7. The intervertebrae implant of claim 6, comprising second stop means for engagement with said projection in said second rotational position of said screw means.

8. The intervertebrae implant of claim 1, comprising at least one aperture provided in said first and second sidewalls.

9. The intervertebrae implant of claim 8, wherein said first and second sidewalls each comprise a plurality of diamond-shaped apertures.

10. The intervertebrae implant of claim 1, wherein said sidewalls have a substantially trapezoidal shape so as to form a truncated wedge-shaped hollow body.

11. The intervertebrae implant of claim 1, wherein said sidewalls are substantially rectangular.

* * * * *

UNITED STATES PATENT AND TRADEMARK OFFICE
CERTIFICATE OF CORRECTION

PATENT NO. : 6,102,949
DATED : August 15, 2000
INVENTOR(S) : Lutz Biedermann and Jurgen Harms It is certified that error appears in the above-indentified patent and that said Letters Patent is hereby corrected as shown below:

On the Title Page, insert

[30]  Foreign Application Priority Data

GERMANY, DECEMBER 3, 1997, 197 53 685.9

Signed and Sealed this

Twenty-fourth Day of April, 2001

Attest:

NICHOLAS P. GODICI

*Attesting Officer*   *Acting Director of the United States Patent and Trademark Office*